US00PP26765P3

(12) United States Plant Patent
Wright et al.

(10) Patent No.: US PP26,765 P3
(45) Date of Patent: May 31, 2016

(54) BLUEBERRY PLANT NAMED 'C03-038'

(50) Latin Name: ***Vaccinium corymbosum* hybrid**
Varietal Denomination: C03-038

(71) Applicants: CostaExchange Pty Ltd., Corindi (AU); Florida Foundation Seed Producers, Inc., Gainesville, FL (US)

(72) Inventors: Gary Wright, Corindi Beach (AU); Paul Lyrene, Micanopy, FL (US)

(73) Assignees: CostaExchange Pty Ltd, Corindi (AU); Florida Foundation Seed Producers, Inc., Marianna, FL (US)

( * ) Notice: Subject to any disclaimer, the term of this patent is extended or adjusted under 35 U.S.C. 154(b) by 13 days.

(21) Appl. No.: 13/999,294

(22) Filed: Feb. 6, 2014

(65) Prior Publication Data

US 2014/0223619 P1 Aug. 7, 2014

Related U.S. Application Data

(60) Provisional application No. 61/849,978, filed on Feb. 6, 2013.

(51) Int. Cl.
*A01H 5/08* (2006.01)

(52) U.S. Cl.
USPC ..... Plt./157
CPC ..... *A01H 5/08* (2013.01)

(58) Field of Classification Search
USPC ..... Plt./157
See application file for complete search history.

(56) References Cited

U.S. PATENT DOCUMENTS

PP12,165 P2 10/2001 Lyrene
PP20,642 P2 1/2010 Wright et al.

OTHER PUBLICATIONS

PLUTO Plant Variety Database 2015.*
Australian plant variety journal 2011 vol. 24 No. 1 published May 13, 2011.*

* cited by examiner

*Primary Examiner* — Annette Para
(74) *Attorney, Agent, or Firm* — Hahn Loeser & Parks, LLP

(57) ABSTRACT

A new and distinct cultivar of blueberry (*Vaccinium corymbosum* hybrid) plant named 'C03-038,' characterized by its semi-upright plant shape and strong plant growth vigor, low chilling requirement, early timing of fruiting, medium fruit size with oblate shape, firm fruit suited to handling, good fruit flavor. This combination results in higher quality fruit with a later availability than other varieties.

5 Drawing Sheets

Latin name of the family, genus and species: Family—Ericaceae. Genus—*Vaccinium.* Species—*corymbosum* hybrid.

Variety denomination: The new blueberry plant claimed is of the variety denominated 'C03-038.'

BACKGROUND OF THE INVENTION

The present invention relates to a new and distinct perennial variety of *Vaccinium corymbosum* hybrid (blueberry), which has been given the variety denomination of 'C03-038.' The new variety 'C03-038' shows distinctive traits such as early season, good flavor and firm fruit. Its market class is that of a fruiting plant. The new variety 'C03-038' is intended for use as fresh fruit for shipping, customer pick and processing markets and as a home garden plant.

The new blueberry cultivar is a selection resulting from seedlings produced in a controlled breeding programme of *Vaccinium* varieties in Florida, USA in 2001 from a cross of the blueberry variety known as 'F93-368' (seed parent) (unpatented) and the blueberry variety known as 'C97-390' (pollen parent) (U.S. Plant Pat. No. 20,642). The seed from the cross was sown and grown in Corindi Beach, New South Wales, Australia. The new cultivar was discovered and selected in 2003 as a single plant within a population of seedlings resulted from the controlled cross, in an experimental block in the field at Corindi Beach, New South Wales, Australia, and has since been named 'C03-038.' Selection criteria were a combination of early season, low chilling requirement, medium fruit of good flavor, firm fruit. The new variety was subsequently evaluated for a number of years at the commercial farm at Corindi Beach, New South Wales, Australia.

Asexual reproduction of the new variety 'C03-038' by softwood cutting propagation since 2003 at Corindi Beach, New South Wales, Australia has demonstrated that the new variety reproduces true to type with all of the characteristics, as herein described, firmly fixed and retained through successive generations of such asexual propagation, with the clones phenotypically identical to the original plant.

The seed parent 'F93-368' is characterized by a medium fruit size and very early to early timing of ripening of fruit. The pollen parent 'C97-390' is characterized by a large fruit size and very early to early timing of ripening of fruit. The new variety 'C03-038' differs from the seed and pollen parents in that 'C03-038' has a later cropping timing compared to both parents and a smaller fruit size compared to the pollen parent. The new variety 'C03-038' has maintained its distinguished characteristics throughout successive asexual propagation.

SUMMARY OF THE INVENTION

The new blueberry variety originated from a cross of 'F93-368' (seed parent) (unpatented) and the variety known as 'C97-390' (pollen parent) (U.S. Plant Pat. No. 20,642) in 2001 in Florida, USA. The seed parent is characterized by a medium fruit size and very early to early timing of ripening of fruit. The pollen parent is characterized by a large fruit size and very early to early timing of ripening of fruit.

The new blueberry variety resulted from seedlings produced in a controlled breeding program. The cross was made in 2001 in Florida, USA and the seed was sown and grown on in Corindi Beach, NSW, Australia.

The new variety was selected in 2003 from among plants located on land at Corindi Beach and has since been named 'C03-038'. Since then plants of 'C03-038' were propagated by cuttings for further evaluation and resulted to be uniform and stable. Asexual reproduction of the new variety 'C03-038' by cutting propagation since 2003 at Corindi Beach, NSW, Australia has demonstrated that the new variety reproduces true to type plants.

The new variety was selected in 2003 as a single plant within a population of seedlings resulting from controlled cross of *Vaccinium* varieties. The seedling population was planted in an experimental block in the field at Corindi Beach, NSW, Australia and the selection of the new variety took place in the same block. Selection criteria were a combination of early season, low chilling requirement, medium fruit of good flavour, elliptic fruit shape and firm fruit. The new variety was subsequently evaluated for a number of years at the commercial farm at Corindi Beach, NSW, Australia.

The following characteristics of the new variety have been repeatedly observed and can be used to distinguish 'C03-038' as a new and distinct variety of *Vaccinium corymbosum* hybrid:

1. low chilling requirement
2. semi-upright habit
3. early fruiting season
4. medium fruit size
5. good flavor
6. firm fruit
7. elliptic fruit shape The new variety differed from the female and male parents ('F93-368' and 'C97-390' respectively) in that 'C03-038' has a smaller fruit size but firmer fruit compared to the male parent 'C97-390'. The new blueberry variety C03-038 has maintained its distinguished characteristics throughout successive asexual propagation. The variety has been repeatedly asexually reproduced thought softwood cuttings in NSW, Australia and the clones are phenotypically identical to the original plant.

BRIEF DESCRIPTION OF THE DRAWINGS

The accompanying photographic illustration shows typical specimens in full color of the foliage and fruit of the new variety 'C03-038.' The colors are as nearly true as is reasonably possible in a color representation of this type.

Figure 1:
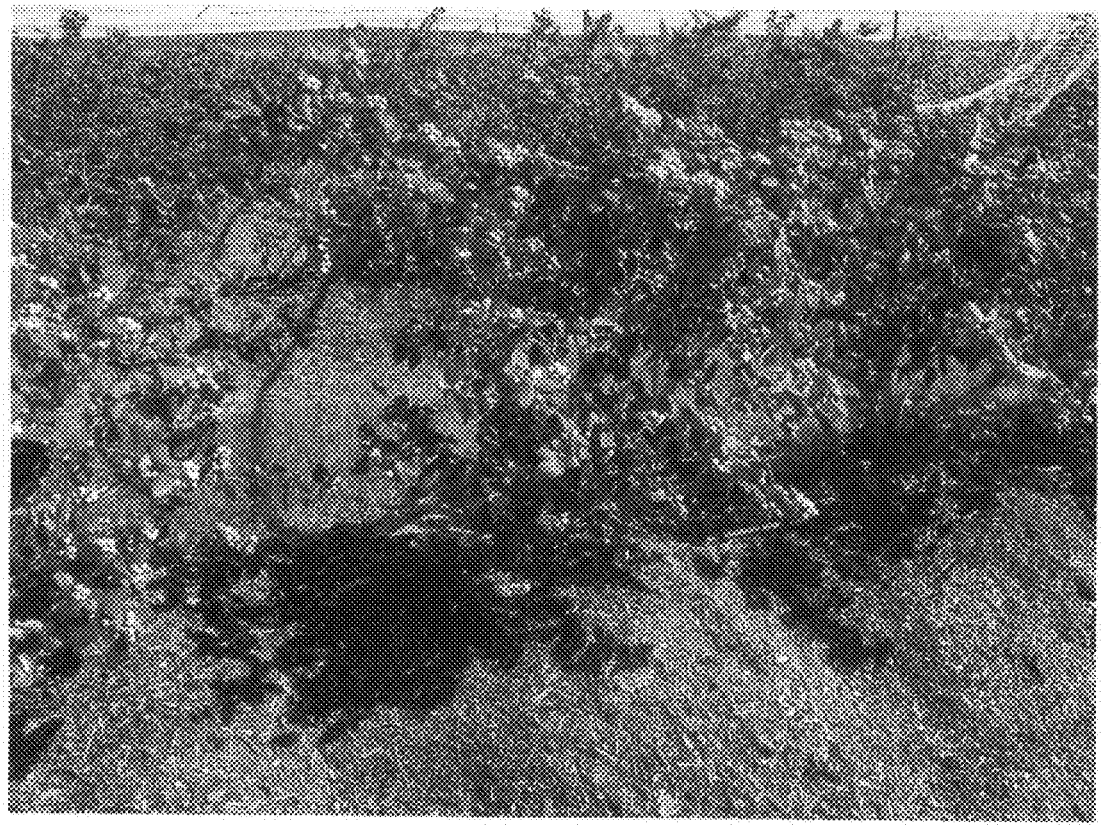
FIG. 1 is a photograph of the new variety 'C03-038' demonstrating the plant's semi-upright growth habit.
Figure 2:
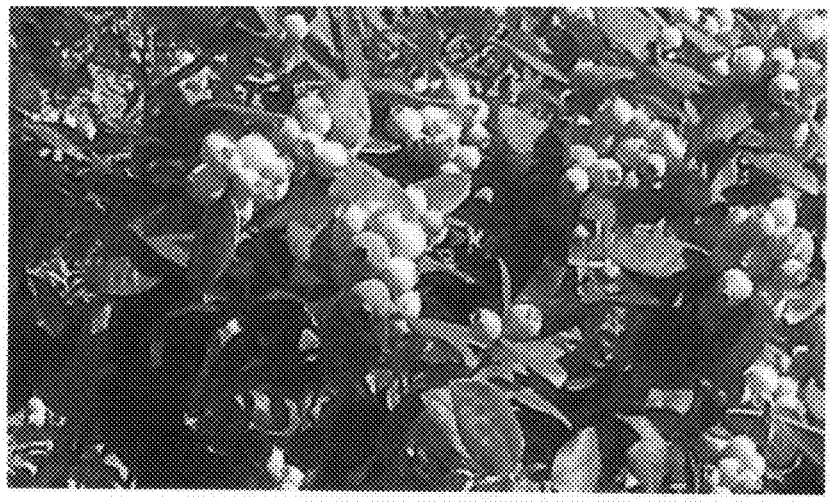
FIG. 2 is a photograph of the fruit of the new variety 'C03-038.'
Figure 3:
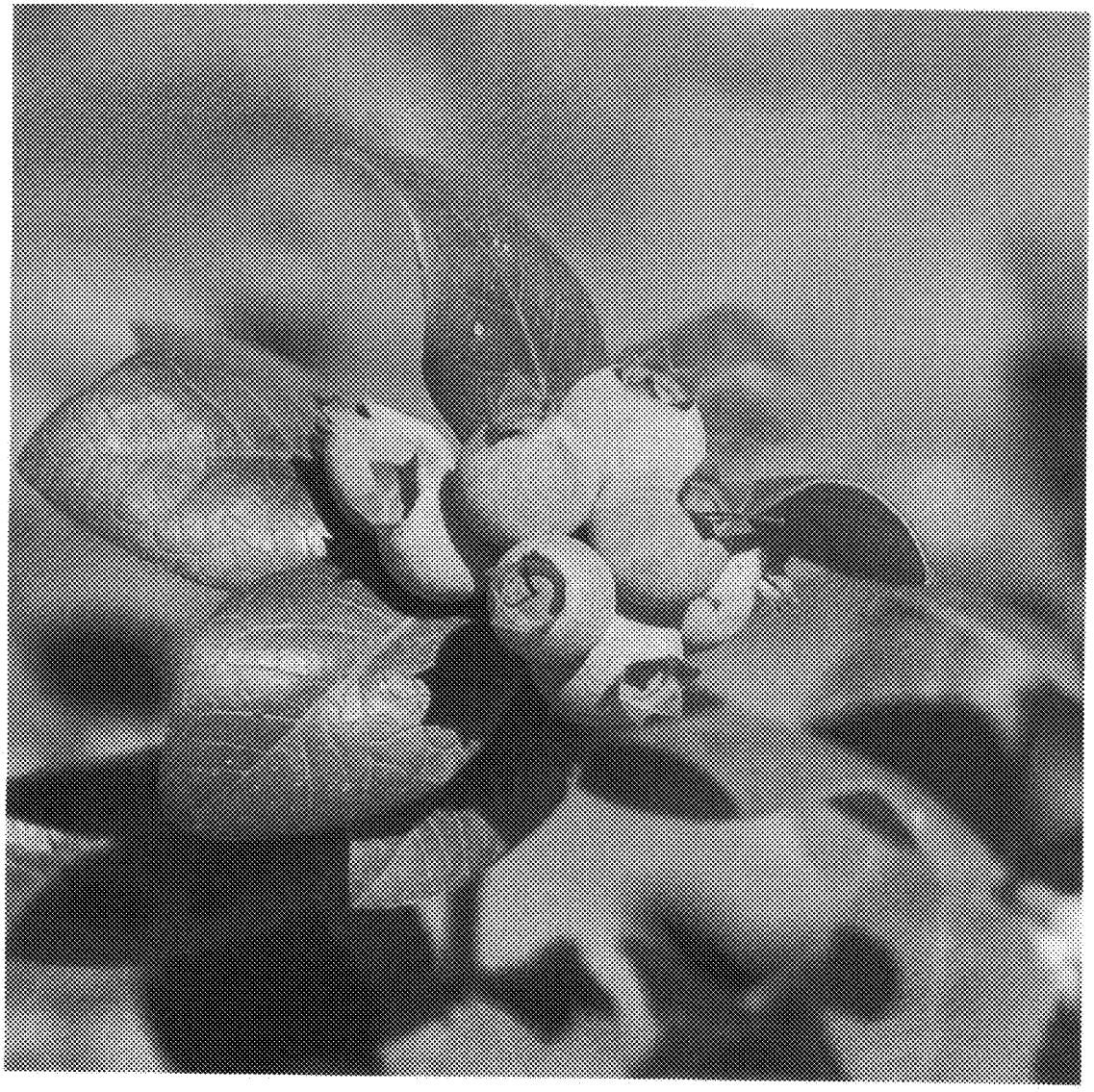
FIG. 3 is a photograph of the green fruit of the new variety 'C03-038.'
Figure 4:
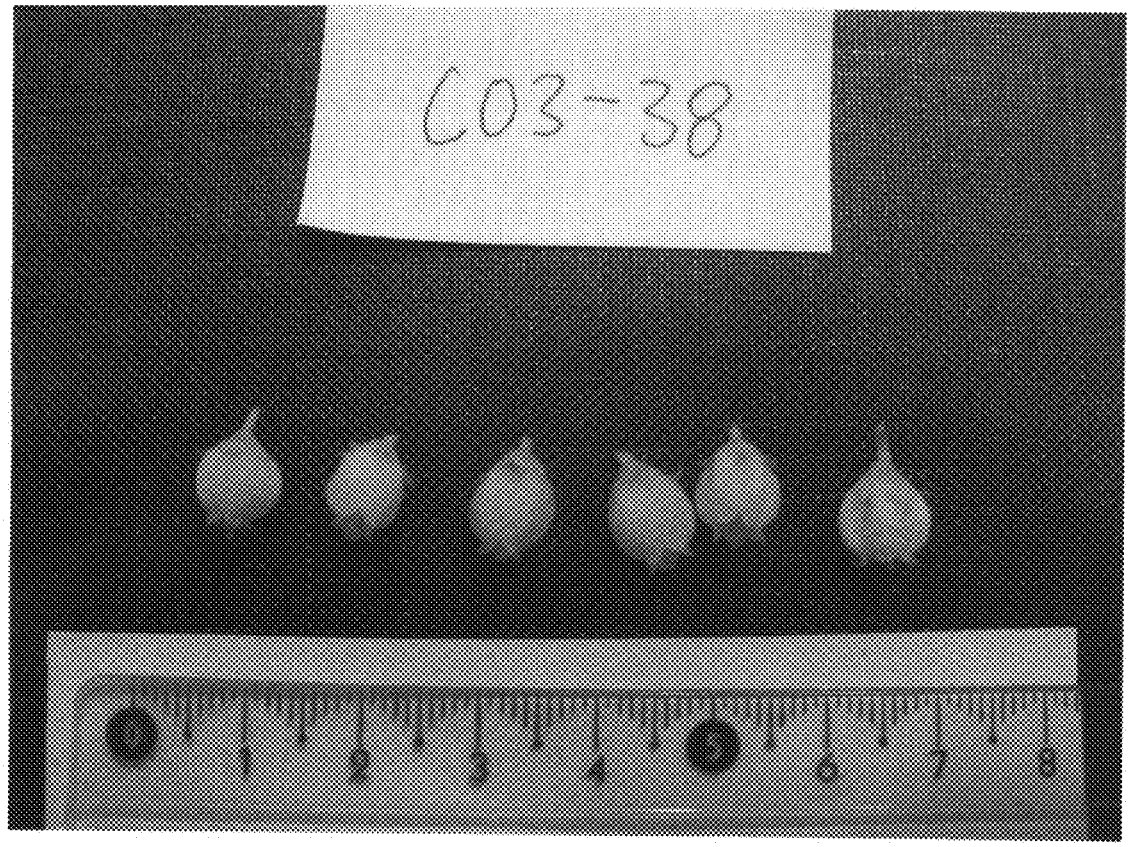
FIG. 4 is a photograph of the flowers of the new variety 'C03-038.'
Figure 5:
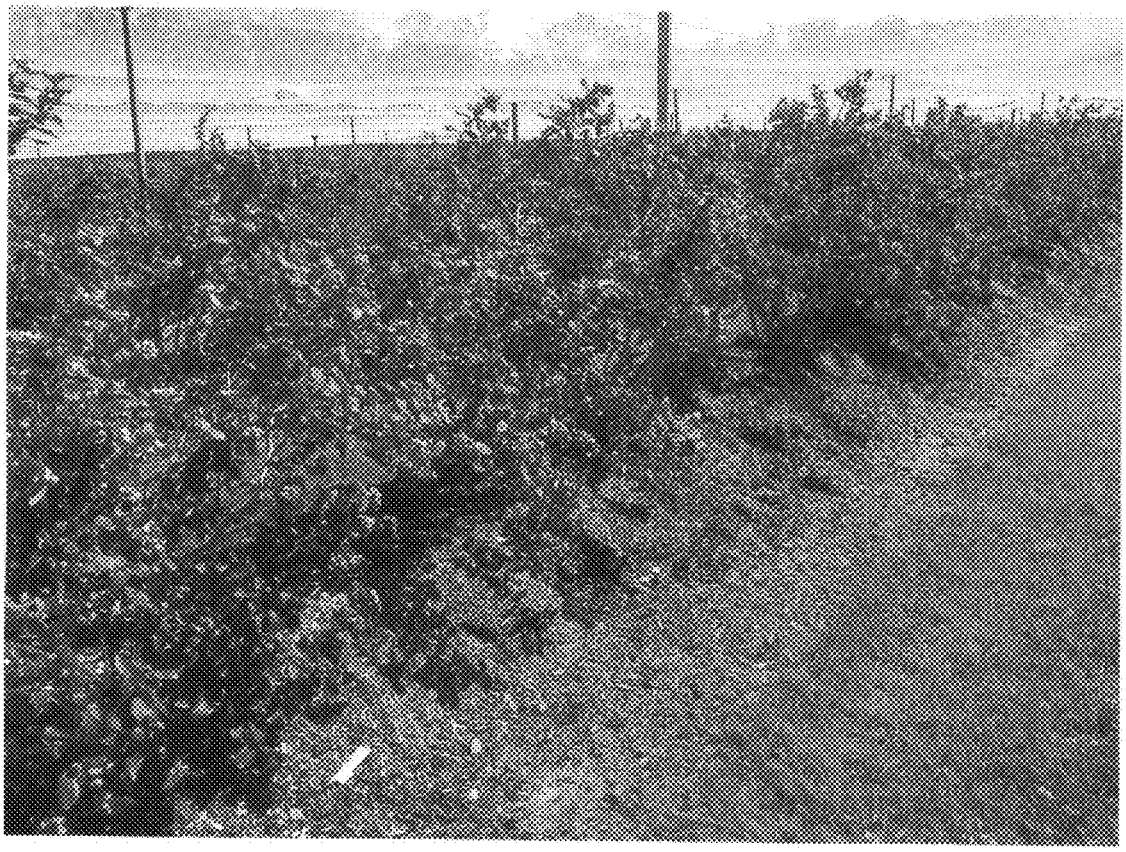
FIG. 5 is a photograph of the new variety 'C03-038' growing in commercial field.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'C03-038.' The data which defines these characteristics was collected from asexual reproductions of the original selection. Dimensions, sizes, colors, and other characteristics are approximations and averages set forth as accurately as possible. The plant history was taken on plants approximately 5 years of age, and the descriptions relate to plants grown in the field in Corindi Beach, New South Wales, Australia. Descriptions of fruit characteristics were made on fruit grown in Corindi Beach, New South Wales, Australia. Color designations are from R.H.S. Chart—edition 2007.

Classification:

*Family*.—Ericaceae.
*Genus*.—*Vaccinium*.
*Species*.—*corymbosum* hybrid.
*Common name*.—Blueberry.

Parentage:

*See Parent*.—F93-368 (unpatented).
*Pollen parent*.—'C97-390' (U.S. Plant Pat. No. 20,642).

Market class: Suitable for the Commercial, Hand Harvest Fresh, Processed, and Home Garden Markets.

PLANT

General:

*Parentage*.—'F93-368'×'C97-390'.
*Plant height*.—1.45 m.
*Plant width*.—1.01 m.
*Growth habit*.—Semi-upright.
*Growth*.—Low vigour.
*Productivity*.—Medium to high.
*Cold hardiness*.—Low.
*Cold tolerance*.—Low to medium.
*Chilling requirement*.—Low chill.
*Tolerance to disease*.—The variety is susceptible to leaf rust.
*Leafing*.—Medium to high. Retains leaves overwinter under the environment at Corindi Beach, NSW, Australia.
*Twigginess*.—High.

STEM

General:

*Suckering tendency*.—Low.
*Mature cane color*.—Between greyed orange group 165A and greyed green group 197A.
*Mature cane length*.—0.8 m.
*Mature cane width*.—9.6 mm.
*Bark texture*.—Smooth.
*Surface texture of new wood*.—Very smooth.
*Internode length on strong, new shoots*.—17.2 mm.
*Fruiting wood*.—16.2 cm in length.

FOLIAGE

General:

*Time of beginning of leaf bud burst*.—End of August average date 28 August, similar to 'C97-390'.

*Leaf color* (*top side*).—Similar to green group 137B and the vein colour similar to yellow-green group N144A.

*Leaf color* (*under side*).—Yellow green group 147B.

*Leaf arrangement*.—Alternate.

*Leaf shape*.—Elliptic.

*Leaf margins*.—Entire.

*Undulation of margin*.—Absent or very weak.

*Leaf venation*.—Reticulate.

*Leaf apices*.—Acute.

*Leaf bases*.—Rounded.

*Leaf length*.—Mean 47.00 mm (45-60 mm range).

*Leaf width*.—Mean 28.00 mm (24-36 mm range).

*Leaf length/width ratio*.—1.7.

*Leaf nectarines*.—Absent.

*Pubescence of upper side*.—Absent.

*Pubescence of lower side*.—Absent.

*Cross sectional profile*.—Flat.

*Longitudinal profile*.—Straight.

*Attitude*.—Horizontal.

Petioles:

*Length*.—Mean 3.1 mm (2-4 range).

*Width*.—1.9 mm.

*Color*.—Yellow green group 145A.

FLOWERS

General:

*Time of beginning of flowering*.—Early.

*Time of* 50% *anthesis*.—Average date 20 July.

*Flower shape*.—Urceolate.

*Flower bud density*.—Medium to dense.

*Flower fragrance*.—Absent.

*Flower arrangement*.—Alternately.

*Flower type*.—Complete flower, having sepals, petals, stamens and pistils.

Corolla:

*Color*.—Green-white group 157D.

*Length*.—6.6 mm.

*Width*.—Mean 7.1.

*Aperture width*.—5.1 mm.

*Anthocyanin coloration of corolla*.—Absent or very weak.

*Corolla ridges*.—Present.

*Protrusion of stigma*.—Present.

*Corolla shape*.—Urceolate.

Inflorescence:

*Length*.—22-31 mm.

*Diameter*.—15-22 mm.

*Length of peduncle*.—17 mm.

*Surface texture of peduncle*.—Smooth.

*Color of peduncle*.—Yellow green group 147D.

*Length of pedicel*.—4.7 mm.

*Surface texture of pedicel*.—Smooth.

*Color of pedicel*.—Yellow green group 147D.

*Number of flowers per cluster*.—4.

*Flower cluster density*.—Sparse.

Calyx (with sepals):

*Diameter*.—6.11 mm.

Stamen:

*Length*.—6.09 mm.

*Number per flower*.—10.

*Filament color*.—Yellow-green group 145D.

*Style*.—Length — 8.3 mm.

*Color*.—Yellow-green group 144C.

Pistil:

*Length*.—11.3 mm.

*Ovary color* (*exterior*).—Green group 143A.

Anther:

*Length*.—3.06 mm.

*Number*.—10.

*Color*.—Greyed-orange group n167B.

Pollen:

*Abundance*.—Abundant.

*Color*.—Yellow group 4D.

*Self-compatibility*.—Possible, but smaller fruit sizes and very few seeds.

FRUIT

General:

*Time of fruit ripening*.—Early season.

*Time of* 50% *maturity*.—Average date 18$^{th}$ September.

*Fruit development period*.—60 days.

*Cluster density*.—Sparse.

*Numbers of berries per cluster*.—4.

*Unripe fruit color*.—Yellow-green group 144A.

*Ripe berry color*.—Violet-blue group 98B.

*Berry surface wax abundance*.—Strong to very strong.

*Berry flesh color*.—Yellow-green group 145C.

*Berry weight*.—Mean 1.6 g (1.2-2.5 range).

*Berry height from calyx to scar*.—13.7 mm.

*Berry diameter*.—14.01 mm.

*Berry shape*.—Elliptic.

*Fruit stem scar*.—Very small and dry.

*Sweetness when ripe*.—Medium to high.

*Firmness when ripe*.—Very firm.

*Acidity when ripe*.—Medium.

*Storage quality*.—Long storage.

*Suitability for mechanical harvesting*.—Not suitable.

*Self-fruitfulness*.—High.

*Uses*.—Fresh.

SEED

General:

*Seed abundance in fruit*.—Medium (166 in 10 fruit).

*Seed color*.—Greyed-orange group 165B.

*Seed length*.—1.94 mm.

COMPARISON BETWEEN PARENTAL AND COMMERCIAL CULTIVARS

| | Variety | Comparator variety | | | | |
|---|---|---|---|---|---|---|
| Characteristic | C03-038 | C99-042 | Emerald | C97-390 | Star | Snow-chaser |
| Soluble solid content (%) | 11.2 | 13.1 | 11.6 | 12.2 | 13.1 | 14.3 |
| Titratable acidity (%) | 0.6 | 0.3 | 0.5 | 0.3 | 0.4 | 0.5 |

-continued

| Characteristic | Variety C03-038 | Comparator variety C99-042 | Emerald | C97-390 | Star | Snowchaser |
|---|---|---|---|---|---|---|
| Fruit weight (g) | 1.6 | 1.9 | 3.0 | 2.0 | 1.9 | 1.7 |
| Fruit shape | elliptic | oblate | oblate | oblate | oblate | oblate |
| Firmness (g/mm) | 300 | 273 | 187 | 211 | 210 | 188 |
| Leaf length (mm) | 47 | 52.5 | 62 | — | 65.7 | 56.1 |
| Leaf width (mm) | 28 | 24.6 | 37 | — | 27.7 | 32.1 |

-continued

| Characteristic | Variety C03-038 | Comparator variety C99-042 | Emerald | C97-390 | Star | Snowchaser |
|---|---|---|---|---|---|---|
| Plant habit | Semi-upright | Semi-upright to spreading | Spreading | Semi-upright | Strongly upright to upright | Semi-upright |
| Time of fruit ripening | Early | Early | Mid to late | Early | Late | Very early |

It is claimed:

1. A new and distinct variety of blueberry plant named 'C03-038,' substantially as illustrated and described herein.

* * * * *